United States Patent [19]

Allen et al.

[11] Patent Number: 4,589,927
[45] Date of Patent: May 20, 1986

[54] LIQUID MULTISOLID FLUIDIZED BED PROCESSING

[75] Inventors: Billy R. Allen, Westerville; William J. Huffman, Worthington; Herman Nack, Columbus, all of Ohio

[73] Assignee: Battelle Development Corporation, Columbus, Ohio

[21] Appl. No.: 615,026

[22] Filed: May 29, 1984

[51] Int. Cl.⁴ .............................. B08J 8/20; B08J 8/32
[52] U.S. Cl. .................................. 134/25.1; 422/140; 422/145; 422/147; 423/DIG. 16; 210/618
[58] Field of Search ............... 422/140, 142, 144, 145, 422/147; 423/DIG. 16; 134/25.1; 210/189, 290, 617, 618, 661, 675, 677

[56] References Cited

U.S. PATENT DOCUMENTS

| | | | |
|---|---|---|---|
| 1,671,864 | 5/1928 | Higgins | 210/661 |
| 3,754,993 | 8/1973 | Oguchi et al. | 210/661 |
| 3,901,660 | 8/1975 | Ohorodnik et al. | 422/140 |
| 4,009,099 | 2/1977 | Jeris | 210/618 |
| 4,016,044 | 4/1977 | Fresnel et al. | 435/3 |
| 4,016,293 | 4/1977 | Coughlin et al. | 426/42 |
| 4,039,290 | 8/1977 | Inada et al. | 422/144 |
| 4,084,545 | 4/1978 | Nack et al. | 110/245 |
| 4,102,786 | 7/1978 | Okada et al. | 210/290 |
| 4,269,716 | 5/1981 | Gurian | 210/675 |

FOREIGN PATENT DOCUMENTS 107153   8/1979   Japan ................................. 210/617

Primary Examiner—David L. Lacey
Attorney, Agent, or Firm—Barry S. Bissell

[57] ABSTRACT

Continuous chemical and biological reactions may be carried out in a liquid fluidized reactor (1). Improved mixing and mass transport between gas/liquid/solid phases is provided by fluidizing large particles (2) with a liquid in a dense bed in the bottom of the reactor (1) while recirculating small entrained particles (3) and the liquid through the reactor (1), particle separator (9), external regenerator (10) and conduits (7) and (8) back through the dense bed of large particles (2).

16 Claims, 1 Drawing Figure

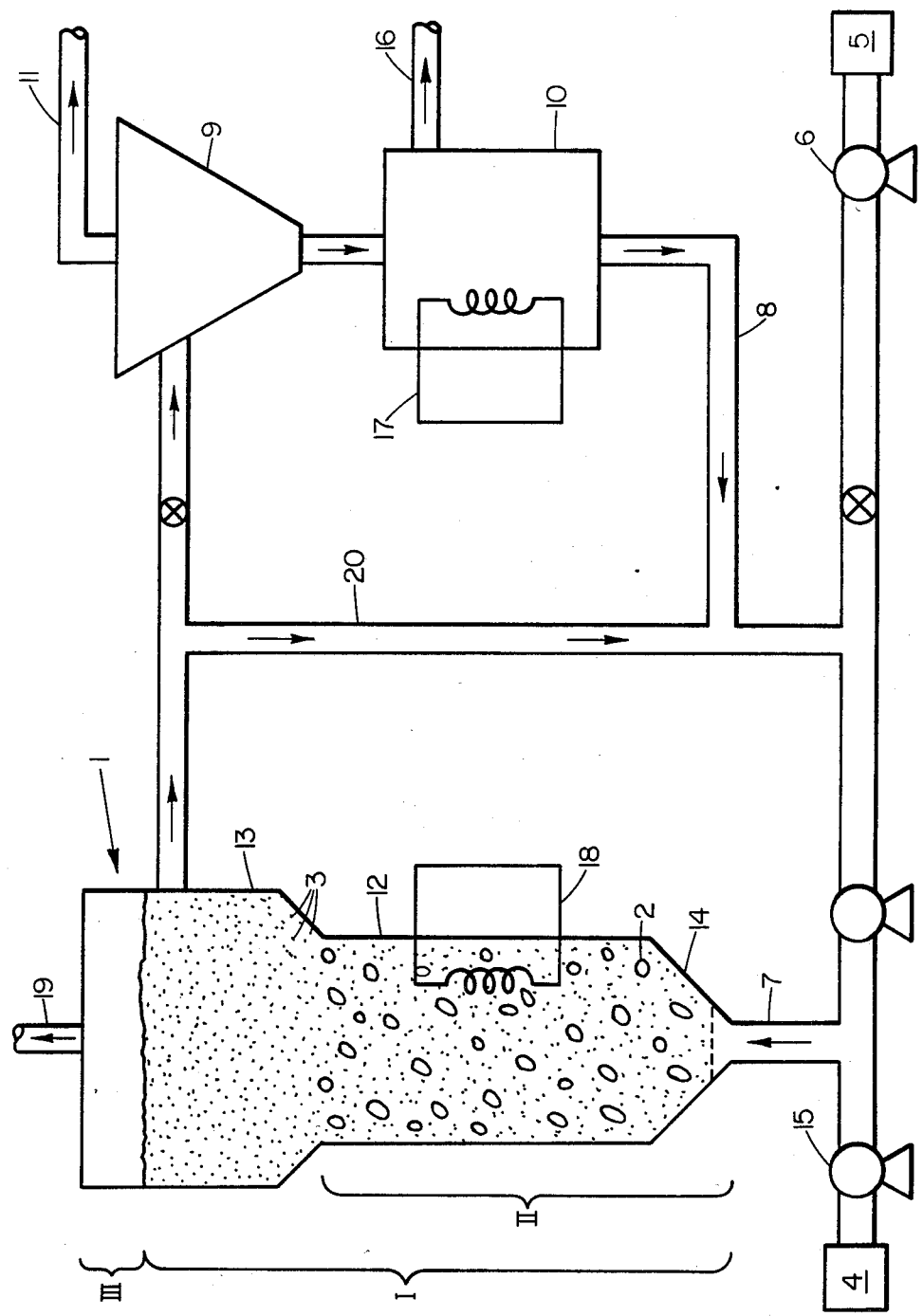

LIQUID MULTISOLID FLUIDIZED BED PROCESSING

TECHNICAL FIELD AND BACKGROUND ART

The invention relates to chemical and biological reactions and, in particular, to a process for making a variety of reactions more productive in either a continuous or a batch mode.

The process is in the field of fluidized bed technology wherein a solid particulate (whether inert or reactive) is fluidized or entrained in a liquid stream. Examples of liquid fluidized beds can be found in the literature. For example, see a review by Allen, et. al., Annals New York Acadamy of Science Biochemical Engineering, Volume 326, pgs. 105–117 (1979). U.S. Pat. Nos. 4,016,293 and 4,016,044 disclose liquid fluidization processes for enzyme-catalyzed reactions. Typically, an enzyme is immobilized on a particle carrier and packed into a reactor. A liquid containing reactants is then used to fluidize the carriers and bring the reactants into contact with the enzyme. The products are removed with the liquid out the top of the reactor while the carriers remain in the bed for continued use. Reaction rates are typically slow in the process and separation of the products from the liquid may be troublesome.

In addition to the background art in liquid fluidization, there is a considerable amount of literature in the area of gas fluidization. In particular, the assignee of the present application owns U.S. Pat. No. 4,084,545 which discloses the use of a dense fluidized bed and an overlapping expanded, entrained bed. However, the liquid fluidized beds present very different problems requiring different solutions as will be shown in more detail below.

SUMMARY OF THE INVENTION

It is an object to provide a continuous process for conducting chemical and biological reactions.

It is another object to provide an extremely efficient process to increase the rates of reaction and/or selectivity.

It is further an object to provide a process whereby the useful products of reactions may be easily separated from the reactants and/or carriers and/or by-products.

In accordance with the objectives, the invention is a liquid fluidization process for improving the rate, efficiency and/or controllability of chemical and biological reactions due to improved contact of liquid, gas and solid phases. The method comprises forming an entrained bed of a relatively fin particle component in a reactor utilizing a liquid fluidization medium and superimposing a dense fluidized bed of relatively coarse particles on the entrained bed in the lower region of the reactor. The liquid fluidization medium is introduced at a rate sufficient to simultaneously fluidize the coarse particles and entrain the fine particles. The fine particles and, at times, the liquid are recirculated out the top of the reactor and back in the bottom. The dense bed of coarse particles encourages improved mixing ∗ and contact of solid, liquid and any gas phases present.

Preferably, the reactants are fed into the reactor in such a manner as to provide thorough mixing of the reactants with the fine and coarse particles resulting in improved reaction yields and rates.

BRIEF DESCRIPTION OF THE DRAWINGS

The FIGURE is a schematic view of apparatus used to practice the inventive method.

DESCRIPTION OF THE PREFERRED EMBODIMENTS

Several states of agitation between particles and fluids are defined in the fluidization art. When a fluid passes uniformly upward in a vessel through a settled bed of finely-divided, solid particles, the condition of the particles depends on the fluid velocity. At low velocities, the bed remains essentially undisturbed as fluid merely percolates through the void space between particles. At a certain higher flow rate, however, particles become buoyant in the fluid stream and are free to move in random motion in all directions. The volume which they occupy expands, but the particles substantially remain in this expanded volume. The accepted technical term for this state is "fluidized". At still higher velocities, the particles are "lifted" or "entrained" in the fluid and are carried to the top and out of the reactor with the fluid.

Apparatus for practicing the method is shown schematically in the FIGURE. It resembles apparatus for gas fluidization. A reactor 1 consists of an elongated vessel having a lower funnel shaped bottom 14, an intermediate constant cross-section center portion 12 and an enlarged region 13, also known as a disengager, on top. A conduit 7 is used to introduce the liquid fluidization medium into the reactor from a source 5 and pump 6 or from the external recycle loop. Liquid, solid or gaseous reactants can be added through source 4, pump 15 and conduit 7.

The liquid fluidization medium is used to entrain a relatively fine particle component 3 throughout a space region I within the reactor and to then recirculate the fine particle component out the top of the reactor to separator 9, external reactor 10 and through conduits 8 and 7 back into the reactor 1.

The liquid fluidization medium is also used to simultaneously fluidize a relatively coarse particle component 2 in a dense bed in a space region II of the reactor. The dense bed is the key to providing improved mixing and contact of liquid, solid and gaseous phases as the liquid and fine particles pass through the dense bed. A screen at the bottom of the reactor may be used to support the large particles when not fluidized. The dense bed particles are fluidized in the space region II due to the enlarged cross-section region 13 (and lower velocity therein) which reduces the coarse particle migration to this region. Heat exchange loop 18 may be used to add or widthdraw heat from the reactor.

Waste gas in the reactor flows to the top of the reactor in region III and may be exhausted from stack 19. Separator 9 is used to separate a liquid by-product or waste stream exiting at 11 from the solids which continue on to the external reactor 10. Liquid may or may not be recirculated with the solids. In the external reactor 10, regeneration of the solids may take place whereby the product is removed at 16 and the regenerated solids are recycled back to the bottom or middle of the reactor 1. The recycled particle stream can be used to control the conditions (e.g., pH, temperature, etc.) above the point of recycle entry into the reactor.

External reactor 10 may regenerate the solids by any useful means, for example by pH control, temperature change, solvent extraction, changing ionic strength or chemical or biological reaction. Heat may be added or removed by means of heat exchange loop 17. We use "regeneration" broadly to mean any method for treating the fine particles and returning them to the reactor. The reaction product may be fully or only partially removed in situ from the particles or the reacted particles themselves may be removed and replaced with fresh (unreacted) particles. The external reactor, therefore, is merely a temporary storage and/or regenerator means for holding and/or removing products from the main reactor so that the reaction therein may proceed.

At least a portion of the slurry may be recycled through by-pass line 20 directly to the bottom or middle of the reactor instead of through the regenerator. This allows the reactor to be run at high flow velocities even though the reactants pass through too quickly to complete reaction. The reactants can make several rapid passes through the reactor before going to the regenerator. Thus the by-pass recycle is a way of increasing efficiency in high flow rate situations and for removing products from the reactor to keep the reaction rate from decreasing.

The combination of the coarse particle dense bed and fine particle entrained bed has been found to improve mass transport between phases. This improvement is an important factor in the improved efficiency of reactions carried out in the reactor. Surprisingly this is not the result of increased residence times for the fine particles on each pass through the reactor as is the case for gas-fluidized multisolid beds. The residence times have been found not to be substantially increased with the dense bed present. Though not clear, increased turbulent mixing may instead provide the explanation for the improved contact.

The particle size and density of the relatively fine and relatively coarse particles are selected along with the superficial liquid velocity such that the larger particles are adequately fluidized in the reactor and the finer particles are entrained and carried out of the reactor. It should be clear that the relative particle sizes and flow rate rater than the absolute sizes and rates are important factors in producing the necessary conditions in the reactor. The superficial liquid velocity must be greater than the minimum fluidization velocity of the larger particles and the entrainment velocity (or the terminal velocity) of the finer particles.

The minimum fluidization velocity of the larger particles can be estimated by the correlations given by Wen and Fan* as follows:

*Wen, C. Y., and Fan, L. S., "Some Ramarks on the Correlation of Bed Expansion in Liquid-Solid Fluidized Beds", I&EC Process Design & Development, vol. 13, pp. 194–196, April, 1974.

$$V_{mf} = \frac{0.00134 \, N_{Ga}^{0.890}}{d_p \, \rho_f} \text{ for } 18 < N_{Ga} < 10^5$$

$$V_{mf} = \frac{0.0426 \, N_{Ga}^{0.602}}{d_p \, \rho_f} \text{ for } N_{Ga} > 10^5$$

where $V_{mf}$ = minimum fluidization velocity, cm/sec $$N_{Ga} = \frac{d_p^3 \, (\rho_p - \rho_f) \, \rho_f g}{\mu^2},$$

dimensionless Galileo number
$d_p$ = particle diameter, cm
$\rho_p$ = particle density, g/cm$^3$
$\rho_f$ = liquid density, g/cm$^3$
$\mu$ = liquid viscosity, g/cm-sec
g = gravitational acceleration, cm/sec$^2$ The entrainment velocity of the finer particles can be estimated from the equations given in text books, such as "Fluidization Engineering" by D. Kunii and O. Levenspiel, Robert E. Krieger Publishing Company, Huntington, N.Y. (1977), as follows:

$$V_t = \frac{g(\rho_s - \rho_f) \, d_p^2}{18\mu} \text{ for } N_{Re} < 0.4$$

$$V_t = \left[ \frac{4(\rho_s - \rho_f)^2 \, g^2}{225 \, \rho_f \mu} \right]^{\frac{1}{3}} d_p \text{ for } 0.4 < N_{Re} < 500$$

where $V_t$ = particle entrainment velocity, cm/sec $$N_{Re} = \frac{d_p \rho_f V_t}{\mu},$$

dimensionless particle Reynolds number

Typically, the superficial fluid velocities could vary over a wide range, for example from 0.01 to 100 cm/sec for liquid and 0.1 to 10 cm/sec for gas. However, we have found that the improvements in gas-liquid mass transfer are greatest at superficial gas velocities below about 0.3 cm/sec. In the liquid-solid mass transfer, we have found that the improvements in mass transort are greater in the laminar flow regime (corresponding to a Reynolds number below about 2100). This corresponds more to a preferred superficial flow velocity below about 5.1 cm/sec in a 4.1-cm ID reactor. Typically a lower limit of about 0.01 cm/sec is practical for good fluidization of minimally sized particles.

Average particle sizes (for similarly dense materials) or average densities (for similarly sized particles) should be sufficiently different for the fine and coarse materials to effect the desired fluidization and entrainment. Preferably, the densities of the particles are substantially equal and the average particle sizes vary by at least about an order of magnitude. Typical sizes for conventional bioreactions might be within the range of 0.01–1 mm for the finer particles and 0.1–25 mm for the coarse particles. A particularly preferred system has fine particles of about 0.05–0.5 mm and coarse particles of about 0.5–5 mm along with a superficial velocity of about 0.05–0.5 cm/sec.

Preferably both particle fractions, but at least the coarser particles, should be substantially physically resistant to attrition and not used up in the process. It is preferred that both fractions take active part in physical or chemical reaction as reactants or catalysts. Some examples of inactive materials are sand, gravel, glass beads, metal beads, metal oxides, gels and plastic beads. Some active materials include catalysts, immobilized or encapsulated biomaterials such as co-factors, antibodies, enzymes, whole cells and yeasts, ion exchange resins, encapsulated solvents, molecular sieves or combinations thereof. The active materials may be used as coatings on appropriately sized carriers or may be encapsulated. The coarse and fine particle components may conveniently be made of the same material.

Fluidization liquids may also be either inert or active. Examples include aqueous solutions, organic solvents, electrolytes, mixtures and numerous reactable liquids.

Solid, liquid or gaseous materials may be added with the liquid fluidization medium or separately. Typically they will be inserted into the dense bed region of the reactor. Gases such as air, nitrogen, helium, argon, carbon dioxide, oxygen, hydrogen, carbon monoxide, chlorine, methane and ethylene are common examples of gases which can be used. At least at low flow rates, the gas does not appear to significantly contribute to the expansion of the dense fluidized bed.

A nonexhaustive list of typical reactions which appear to be candidates for improvement when carried out according to the method include whey treatement/lactose hydrolysis, waste treatement, milk coagulation/protein hydrolysis, starch hydrolysis, glucose isomerization, raffinose hydrolysis, solubilization of particulate substrates, amino acid production, keto acid production and synthesis of tertiary amine drug metabolites, antibiotics production, biotransformation products (such as steroid hormones), hydrogenation, coal liquifaction, leaching of ores and production of enzymes or gene products (such as proteins, peptides and vaccines).

EXAMPLES OF THE INVENTION

In situ removal of the products and by-products of reactions to keep the rate of reaction from decreasing is a primary advantage of the inventive process that can be realized at any flow velocity. Other advantages are dependent on the flow rate as will be seen in the following examples.

EXAMPLE 1

Bed Residence Time

A sharp contrast between a liquid multisolid process and a gaseous multisolid process occurs in the effect of the dense bed on particle residence time in the reactor. In the gas fluidized system the resident time of the entrained bed particles is substantially increased when the coarse particle dense fluidized bed is present. This accounts for improved reaction parameters in the system.

The liquid fluidized dense bed, however, does not appear to increase the residence time of entrained bed particles suggesting, therefore, that little benefit in reaction efficiency could be gained in such a system.

The results of an experiment to find the effect of the dense bed on entrained bed residence time (which is proportional as the total volume of particles in the reactor at a given time) are shown in Table 1. Apparatus, such as shown in the FIGURE, was constructed for the study. The reactor consisted of a 7.6 cm ID transparent plastic pipe with an overall effective height of 165 cm. The bottom of the reactor was reduced by a 60-degree cone and connected to a 1.9 cm tee, which served as the inlet for recycled water. Water and entrained solids were circulated between the reactor and an external surge tank. A water-cooled heat exchanger was provided in the surge tank to dissipate the heat generated in the circulation pump and thereby maintain a constant temperature in the circulating slurry.

An ion exchange resin (Duolite A-109, Diamond Shamrock/Duolite International) was used as the circulating solids. Glass beads (¼-inch diameter) were used for the dense bed.

TABLE 1

EFFECT OF DENSE BED ON ENTRAINED BED HOLD-UP

| Dense Bed Volume, ml[a] | Water Recycle Rate, liters/min | Air Flow Rate liters/min | Entrained Bed Hold-up, ml[b] |
|---|---|---|---|
| 0 | 38 | 0.26 | 208 |
| 350 | 38 | 0.26 | 230 |
| 700 | 38 | 0.26 | 207 |
| 1050 | 38 | 0.26 | 211 |
| 0 | 38 | 1.94 | 260 |
| 350 | 38 | 1.94 | 230 |
| 700 | 38 | 1.94 | 226 |
| 1050 | 38 | 1.94 | 210 |
| 0 | 76 | 0.26 | 240 |
| 350 | 76 | 0.26 | 230 |
| 700 | 76 | 0.26 | 187 |
| 1050 | 76 | 0.26 | 180 |
| 0 | 76 | 1.94 | 237 |
| 350 | 76 | 1.94 | 210 |
| 700 | 76 | 1.94 | 208 |
| 1050 | 76 | 1.94 | 180 |

[a] Static volume
[b] Wet basis

The results actually show a reduction in residence time when the dense bed is present. This is in sharp contrast to behavior in a gas-fluidized multisolid system and would support no improvement in efficiency of reactions carried out in the bed.

EXAMPLE 2

Gas/Liquid Mass Transfer

The same apparatus used in Example 1 was used to determine the effect of dense bed on gas/liquid mass transfer rates. In this experiment the mass transfer was determined for oxygen moving from injected air to the liquid phase.

Oxygen transfer tests were run separately with only the dense bed or the entrained bed and then jointly. The tests were conducted by first introducing either or both of the bed particles into the bottom of the reactor and then fluidizing with water. The system was then sparged with nitrogen to strip off oxygen. When the oxygen concentration was lowered to below 2 ppm, nitrogen was switched to air to start the tests. Oxygen concentration was monitored as a function of time in the surge tank with an oxygen sensor. At the end of each test, the water was sparged again with nitrogen to remove the oxygen for the next test.

Test conditions are summarized below:
Total volume of water in the system: 68 liters
Total volume of resin (wet basis): 0 or 2000 ml
Dense bed volume (settled): 0 or 1050 ml
Water circulation rate: 38 or 76 liters/min
Air flow: 0.26, 0.76 or 1.94 l/min
Temperature of the water: 28–29 C.

TABLE 2

Dense Bed Effects on Absorption of Oxygen from Air to Water

| Trial | System | Water Recycle l/min | Air Flow l/min | Elapsed Time (sec) to Reach Oxygen Concentration from 2 ppm | | | | |
|---|---|---|---|---|---|---|---|---|
| | | | | 3 ppm | 4 ppm | 5 ppm | 6 ppm | 6.5 ppm |
| 1A | W | 38 | 0.26 | 121 | 243 | 395 | 625 | 842 |
| 1B | W + EB | 38 | 0.26 | 123 | 257 | 439 | 720 | 980 |
| 1C | W + DB | 38 | 0.26 | 115 | 235 | 395 | 640 | — |
| 1D | W + EB + DB | 38 | 0.26 | 82 | 170 | 288 | 470 | 630 |
| 2A | W | 38 | 0.77 | 94 | 186 | 305 | 488 | 637 |

TABLE 2-continued
Dense Bed Effects on Absorption of Oxygen from Air to Water

| Trial | System | Water Recycle 1/min | Air Flow 1/min | Elapsed Time (sec) to Reach Oxygen Concentration from 2 ppm | | | | |
|---|---|---|---|---|---|---|---|---|
| | | | | 3 ppm | 4 ppm | 5 ppm | 6 ppm | 6.5 ppm |
| 2B | W + EB | 38 | 0.77 | 94 | 189 | 314 | 509 | 700 |
| 2C | W + DB | 38 | 0.77 | 85 | 175 | 290 | 455 | 600 |
| 2D | W + EB + DB | 38 | 0.77 | 60 | 135 | 229 | 368 | 490 |
| 3A | W | 38 | 1.94 | 68 | 133 | 218 | 346 | 447 |
| 3B | W + EB | 38 | 1.94 | 66 | 136 | 224 | 361 | 478 |
| 3C | W + DB | 38 | 1.94 | 83[a] | 117 | 195 | 320 | 420 |
| 3D | W + EB + DB | 38 | 1.94 | 51 | 107 | 180 | 286 | 385 |
| 4A | W | 76 | 0.26 | 120 | 259 | 440 | 735 | 998 |
| 4B | W + EB | 76 | 0.26 | 101 | 224 | 396 | 673 | 935 |
| 4C | W + DB | 76 | 0.26 | 100 | 235 | 430 | 735 | — |
| 4D | W + EB + DB | 76 | 0.26 | 55 | 122 | 212 | 350 | 482 |
| 5A | W | 76 | 0.77 | 69 | 146 | 249 | 397 | 522 |
| 5B | W + EB | 76 | 0.77 | 62 | 140 | 240 | 401 | 560 |
| 5C | W + DB | 76 | 0.77 | 73 | 155 | 265 | 420 | 550 |
| 5D | W + EB + DB | 76 | 0.77 | 42 | 101 | 174 | 280 | 400 |
| 6A | W | 76 | 1.94 | 41 | 87 | 142 | 220 | 278 |
| 6B | W + EB | 76 | 1.94 | 40 | 91 | 155 | 246 | 329 |
| 6C | W + DB | 76 | 1.94 | 46 | 88 | 152 | 241 | 309 |
| 6D | W + EB + DB | 76 | 1.94 | 32 | 74 | 130 | 217 | 287 |

[a]elapsed time for 3.5 ppm $O_2$
W = water; EB = Entrained Bed; DB = Dense Bed

The results are shown in Table 2. The expansion of the dense bed increased with the water flow rate but was fairly independent of the air flow rate. The expansions relative to settled bed height were approximately 30 percent at a water flow rate of 38 liters/min and 350 percent at 76 liters/min.

The results show little effect of the entrained bed alone or the dense bed alone on oxygen transfer, especially at lower gas flow rates. The combination of the entrained bed and dense bed, however, greatly improved transfer. This is even more clearly shown in Table 3, which shows oxygen-transfer rate in terms of gas-liquid mass-transfer coefficients derived from the data of Table 2 as follows:

$$K_L a = \frac{R}{C^* - C}$$

where
$K_L a$ = gas-liquid mass-transfer coefficient, $hr^{-1}$
R = oxygen transfer rate, g/L.hr
C = dissolved oxygen concentration in water, g/L
$C^*$ = equilibrium dissolved oxygen concentration of oxygen in water, g/L

TABLE 3
GAS-LIQUID MASS-TRANSFER COEFFICIENTS

| Trial | System | Superficial Water Velocity, cm/sec | Superficial Air Velocity, cm/sec | Gas-Liquid Mass Transfer Coefficient, $hr^{-1}$ |
|---|---|---|---|---|
| 1A | W | 14.0 | 0.10 | 6.8 |
| 1B | W + EB | 14.0 | 0.10 | 6.0 |
| 1C | W + DB | 14.0 | 0.10 | 6.7 |
| 1D | W + EB + DB | 14.0 | 0.10 | 9.1 |
| 2A | W | 14.0 | 0.28 | 8.7 |
| 2B | W + EB | 14.0 | 0.28 | 8.4 |
| 2C | W + DB | 14.0 | 0.28 | 9.2 |
| 2D | W + EB + DB | 14.0 | 0.28 | 11.4 |
| 3A | W | 14.0 | 0.71 | 12.3 |
| 3B | W + EB | 14.0 | 0.71 | 11.7 |
| 3C | W + DB | 14.0 | 0.71 | 13.1 |
| 3D | W + EB + DB | 14.0 | 0.71 | 14.7 |
| 4A | W | 28.0 | 0.10 | 5.8 |
| 4B | W + EB | 28.0 | 0.10 | 6.4 |
| 4C | W + DB | 28.0 | 0.10 | 5.9 |
| 4D | W + EB + DB | 28.0 | 0.10 | 12.1 |
| 5A | W | 28.0 | 0.28 | 10.6 |
| 5B | W + EB | 28.0 | 0.28 | 10.7 |
| 5C | W + DB | 28.0 | 0.28 | 10.0 |
| 5D | W + EB + DB | 28.0 | 0.28 | 14.9 |
| 6A | W | 28.0 | 0.71 | 18.9 |
| 6B | W + EB | 28.0 | 0.71 | 16.9 |
| 6C | W + DB | 28.0 | 0.71 | 17.7 |
| 6D | W + EB + DB | 28.0 | 0.71 | 19.7 |

EXAMPLE 3

Liquid/Solid Mass Transfer

A continuous flow reactor such as shown in the FIGURE was constructed of 4.1 cm ID transparent plastic pipe with an effective height of 457 cm and a working volume of 6,000 $cm^3$. The bottom reduced to a 1.58 cm I.D. pipe to which feed lines for the adsorbate, fluidization medium and fine particle bed were attached. The adsorbate and adsorbent slurry were therefore premixed before introduction. In the experiments the slurry was sampled at the outlet (top) of the reactor for determination of adsorption rate.

Tests were run on adsorption of phenol, using 2-mm or 0.6 mm glass beads as the relatively coarse component of the dense bed and minus 200 mesh (standard) activated carbon as the relatively fine entrained bed. Adsorption tests on phenol were run at a pH of 11.1 in a 0.05M sodium carbonate solution using tap water.

Test results were analyzed based on mass-transfer coefficient derived from steady-state material balance and adsorption isotherm equations shown below:

$$GC_1 \frac{dy}{dz} + (K_L a)(pC_2 E)(y - y^*) = 0 \quad (1)$$

$$GC_2 \frac{dx}{dz} - (K_L a)(pC_2 E)(y - y^*) = 0 \quad (2)$$

$$y^* = mx + b \quad (3)$$

Equations (1) and (2) represent material balances on the adsorbate in the fluid phase and the adsorbent phase, respectively. Equation (3) represents a linear approximation of the adsorption isotherm in the concentration range of the tests. The equation derived for the mass-transfer coefficient by solving the simultaneous differential equations was $$K_L a = \quad (4)$$

-continued $$\frac{GC_1}{E\rho L(C_2 - mC_1)} \log_e \left[ \frac{y_oC_2 - bC_2}{mC_1y_L - mC_1y_o + C_2y_L - bC_2} \right]$$

where
- $K_La$ = mass-transfer coefficient, 1/sec
- G = mass velocity of total feed, g/(sec)(cm$^2$)
- $C_1$ = mass fraction of fluid in the slurry, g/g
- $C_2$ = mass fraction of adsorbent in the slurry, g/g
- E = volume fraction of liquid phase in the adsorption column, cm$^3$/cm$^3$
- $\rho$ = density of adsorbent slurry, g/cm$^3$
- y = mass fraction of adsorbate in fluid, g/g
- x = mass fraction of adsorbate in adsorbent, g/g
- m = a constant appearing in Equation (3), g adsorbent/g fluid
- b = a constant appearing in Equation (3), g adsorbate/g fluid
- L = height of adsorption column, cm
- $y_o$ = Y at adsorption column inlet
- $y_L$ = y at adsorption colum outlet
- z = distance above adsorption column inlet, cm.

Equation (4) represents an approximation of the absolute value of the mass-transfer coefficient, but we believe it is accurate for purposes of comparison of the mass transfer under various conditions of the experiments carried out.

Test conditions and results obtained from the adsorption experiments are reported in Table 4. Tests were carried out with and without the dense bed to determine the effect of the dense bed on the mass-transfer coefficients. Tests were also carried out in both the turbulent and laminar flow regimes. The results from the phenol adsorption tests show that the dense bed has only a modest effect on the phenol mass-transfer coefficient at high liquid flow through the reactor (Tests 4-1 and 4-2), but a large effect at low flow rates (Tests 4-3 through 6-5).

process to produce a fructose syrup. An entrained bed of a suitable resin would be circulated to capture or scavenge hydrogen peroxide and prevent the peroxide from destroying the oxidase. The entrained resin and liquid leave the dense-bed reactor and enter a hydrocyclone where the entrained resin solid is separated from the gas and liquid phases. The gas and liquid would be transported to other process and/or recirculated to the feed. The solid resin would pass to an entrained-bed external reactor where the adsorbed hydrogen peroxide would be reacted. The peroxide reaction could include one of a number of possible reactions; for example, an allyl alcohol will react with the adsorbed peroxide to produce glycidol and glycerol. Once the reaction has taken place, the resin is effectively regenerated and can be returned to the immobilized enzymatic reactor to restart the cycle.

In other cases, the immobilized enzyme could be one for producing a desired product such as acetaldehyde from ethanol using an alcohol oxidase. The hydrogen peroxide would then be removed from the aqueous broth using the same resin as above. Conversely, the entrained-bed, hydrogen peroxide scavenger resin could also be replaced with another immobilized enzyme such as a peroxidase or catalase which converts the peroxide to water or water and oxygen.

Whole Cell Reaction, Scavenging, and/or Recovery

The above example would also apply to immobilized whole cells or yeasts or other microorganisms wherein a product or undesired component is removed from the biological broth, for example, the removal of an antibiotic using an ion-exchange resin. The adsorbed antibiotic would be desorbed in the entrained-bed reactor by effecting a pH change. The resin would then be recycled.

In other applications, the entrained-bed phase could also be, for example, an immobilized antibody to remove a vaccine or antibiotic or other proteins from the

TABLE 4

| | PHENOL ADSORPTION ON ACTIVATED CARBON[a] | | | | | | | | |
|---|---|---|---|---|---|---|---|---|---|
| | Mass Velocity | | | Dense Bed (Glass Beads)[b] | | | Volume | Phenol | Mass |
| | of Total Feed (G), | Column Reynolds | Temperature | Size, | Qty, | Static Height, | Expanded Height, | Fraction of Liquid (E), | Concentration, g/L | Transfer Coefficients |
| Test | g/(sec)(cm$^2$) | Number | °C. | mm | kg | cm | cm | cm$^3$/cm$^3$ | Inlet  Outlet | (sec)$^{-1}$ |
| 4-1 | 13.4 | 5,500 | 13 | 2 | 2.08 | 98 | 425 | 0.863 | 0.0800  0.0567 | 29.7 |
| 4-2 | 13.4 | 5,500 | 15 | — | — | — | — | 1 | 0.0824  0.0577 | 26.8 |
| 4-3 | 3.89 | 1,600 | 15 | 0.6 | 1.97 | 97 | 423 | 0.869 | 0.0636  0.0389 | 14.7 |
| 4-5 | 3.76 | 1,600 | 21 | 2 | 6.44 | 304 | 377 | 0.574 | 0.0638  0.0429 | 15.1 |
| 6-1 | 3.85 | 1,600 | 21 | — | — | — | — | 1 | 0.0840  0.0636 | 5.6 |
| 6-2 | 3.83 | 1,600 | 21 | — | — | — | — | 1 | 0.0676  0.0584 | 2.1 |
| 6-3 | 3.82 | 1,600 | 19 | — | — | — | — | 1 | 0.0600  0.0494 | 3.6 |
| 6-5 | 4.69 | 1,900 | 12 | 2 | 6.57 | 310 | 410 | 0.570 | 0.0530  0.0354 | 19.6 |

[a]Calgon Type BL, pulverized; pH of fluid maintained at 11.1 ± 0.1 using 0.05 M Na$_2$CO$_3$ in tap water; L = 457 cm; $C_1$ = 0.9995 g/g; $C_2$ = 0.0005 g/g; M = 0.0005 g/g; b = 0 g/g; $\rho$ = 1.0 g/cm$^3$
[b]Specific gravity of 2.52.

EXAMPLES 4–6

Useful Reactions

The following examples are hypothetical representations of how we believe conventional processes would be made continuous with the present invention.

Enzymatic Reaction, Scavenging, and/or Recovery

An immobilized oxidase enzyme, for example pyranose-2-oxidase, could be used as the dense-bed phase. Water and glucose would be fed to the dense-bed reactor along with oxygen (or air) to effect the production of an oxidized form of glucose which is used in another fermentation broth. The protein product would be desorbed and would exit the external regenerator vessel by effecting a pH change. The immobilized antibody would then be recycled to the dense-bed reactor.

In another application, an immobilized yeast or bacterial fermentation may be used to produce an alcohol such as ethanol or butanol; such products are well known for inhibiting the fermentation at concentrations exceeding about 1 to 2 percent (by volume) in the broth. The entrained bed might be an encapsulated solvent (microbeads) which is insoluble in water or beads of solid organic known to preferentially adsorb ethanol or butanol from water. The distribution of ethanol between the aqueous broth and the solid organic or encapsulated solvent would not have to be as great as might be expected because the process concept could be used with very high entrained-bed recirculation rates. The desorption in the external entrained-bed regenerator could be accomplished by heating to desorb the more volatile ethanol or butanol. The same approach could be used for other fermentations such as those used to produce mixed products, for example acetone-butanol using dehydrogenase enzymes or the mechanism thereof contained in yeasts or bacteria.

Organic Synthesis Via Catalysis

Numerous examples exist for chemical or petrochemical purposes. Some of these include methanol synthesis, hydrogenation, etc. Consider hydrogenation of organic acids that may be derived from coal or biomass processes. Specifically, it is known that ruthenium is a very effective catalyst for hydrogenating organic acids (e.g., acetic acid, propionic acid, etc.) to the corresponding alcohols. Thus, for the multisolid process, a heterogeneous ruthenium catalyst could act as a dense bed. In the dense-bed reactor with hydrogen addition, the desired reaction would take place. High-rate mixing and interaction of solids with gas would minimize diffusional resistances and assure effective reactions. The entrained bed could be sand or another inert material which would act as a heat adsorber during the exothermic hydrogenation reaction. The entrained sand would be separated in a cyclone (gas-solid phase) and the solid transferred to the external regenerator vessel where heat exchange occurs. The advantage of a multisolid process in this case would be to accomplish heat transfer in a nonreaction atmosphere to prevent excessive corrosion/erosion of heat exchanger tubes while achieving highly effective heat transfer that is well known to exist for fluidized beds.

We claim:

1. A method for improving contact of liquid and solid phases in a reactor comprising;
   introducing a liquid fluidization medium into a lower region of the reactor,
   forming an entrained fluidized bed of a first relatively fine, solid particles with the liquid fluidization medium in a first space region within the reactor,
   forming a dense fluidized bed of a second, relatively coarse solid particle component with the liquid fluidization medium in a more limited space region within the first space region, and
   recirculating the first relatively fine particles from an upper region of the first space region through the dense fluidized bed in the more limited space region.

2. The method of claim 1 further comprising promoting a high efficiency physical or chemical reaction involving at least one reactant by feeding the at least one reactant into the reactor in such manner as to provide thorough mixing of the at least one reactant and the fine and coarse particles.

3. The method of claim 2 wherein the fine particles and/or the coarse particles comprise a material which catalyzes the reaction of the at least one reactant.

4. The method of claim 2 for promoting high efficiency reactions further comprising introducing a gaseous reactant into the lower region of the reactor.

5. The method of claim 4 wherein the superficial gas velocity of the gas reactant is below about 0.3 cm/sec.

6. The method of claim 2 for promoting high efficiency reactions wherein the average particle size of the coarse particle component is at least about 10 times the average particle size of the fine particle component.

7. The method of claim 6 wherein the coarse particles are in the size range of about 0.1–25 mm and the fine particles are in the size range of about 0.01–1 mm.

8. The method of claim 7 wherein the coarse and fine particles are in the size range of 0.5–5 mm and 0.05–0.5 mm respectively.

9. The method of claim 2 wherein the coarse and fine particle components are made of the same material.

10. The method of claim 2 wherein the coarse particles are substantially resistant to attrition and are not used up during the reaction.

11. The method of claim 2 wherein both the fine particles and coarse particles are selected from the group consisting of reactants, catalysts, and sorbents.

12. The method of claim 2 which further comprises lowering the superficial liquid velocity in an upper region of the reactor by means of an enlarged cross-sectional area section such that the dense fluidized bed is contained substantially below such upper region.

13. The method of claim 2 which further comprises reacting the fine particles with the at least one reactant in the reactor, recirculating at least a portion of the fine particles and any products of reaction through an external regenerator and separating the products of reaction and regenerating the fine particles in the regenerator.

14. The method of claim 13 which further comprises adding or withdrawing heat from the regenerator by means of heat exchange elements.

15. The method of claim 1 wherein the liquid fluidization medium is a reactant.

16. The method of claim 15 wherein the super ficial flow velocity of the liquid is in the range of about 0.01–5.1 cm/sec.

* * * * *